United States Patent
Howell

[11] Patent Number: 5,300,077
[45] Date of Patent: Apr. 5, 1994

[54] METHOD AND INSTRUMENTS FOR ACL RECONSTRUCTION

[75] Inventor: Stephen M. Howell, Elk Grove, Calif.

[73] Assignee: Arthrotek, Ontario, Calif.

[21] Appl. No.: 20,901

[22] Filed: Feb. 23, 1993

Related U.S. Application Data

[63] Continuation of Ser. No. 552,815, Jul. 16, 1990, abandoned.

[51] Int. Cl.⁵ .................................................. A61B 17/00
[52] U.S. Cl. ..................................... 606/96; 606/79; 606/98
[58] Field of Search ................................. 606/87-89, 606/96-98; 623/13

[56] References Cited

U.S. PATENT DOCUMENTS

| 4,257,411 | 3/1981  | Cho           | 606/96 |
| 4,541,424 | 9/1985  | Grosse et al. | 606/98 |
| 4,708,139 | 11/1987 | Dunbar        | 606/96 |
| 4,739,751 | 4/1988  | Sapega et al. | 606/88 |
| 4,781,182 | 11/1988 | Purnell et al.| 606/96 |
| 4,787,377 | 11/1988 | Laboureau     | 606/96 |
| 4,823,780 | 4/1989  | Odensten et al.| 606/96 |
| 4,901,711 | 2/1990  | Goble et al.  | 606/98 |
| 4,911,153 | 3/1990  | Border        | 606/98 |
| 4,920,958 | 5/1990  | Walt et al.   | 606/96 |
| 4,945,904 | 8/1990  | Bolton et al. | 606/96 |
| 5,112,335 | 5/1992  | Laboreau et al.| 606/88 |
| 5,112,337 | 5/1992  | Paulos et al. | 606/98 |
| 5,139,520 | 8/1992  | Rosenberg     | 606/87 |

FOREIGN PATENT DOCUMENTS

| 0350780 | 1/1990 | European Pat. Off. | 606/96 |
| 2747568 | 4/1979 | Fed. Rep. of Germany | 606/96 |
| 1448111 | 9/1976 | United Kingdom | 606/96 |

Primary Examiner—Stephen C. Pellegrino
Assistant Examiner—Glenn K. Dawson
Attorney, Agent, or Firm—Harness, Dickey & Pierce

[57] ABSTRACT

A drilling system for ACL reconstruction including: a first drill guide having an aimer member with a notched top surface for mating with the roof of the intercondylar notch; a positioning member having a removable drill guide sleeve; and a second drill guide including a second aimer member with a curved tip and a top notch. The positioning member can be placed on both drill guides for properly positioning the drill guide sleeve for the drilling of both the tibia and the femur.

14 Claims, 9 Drawing Sheets

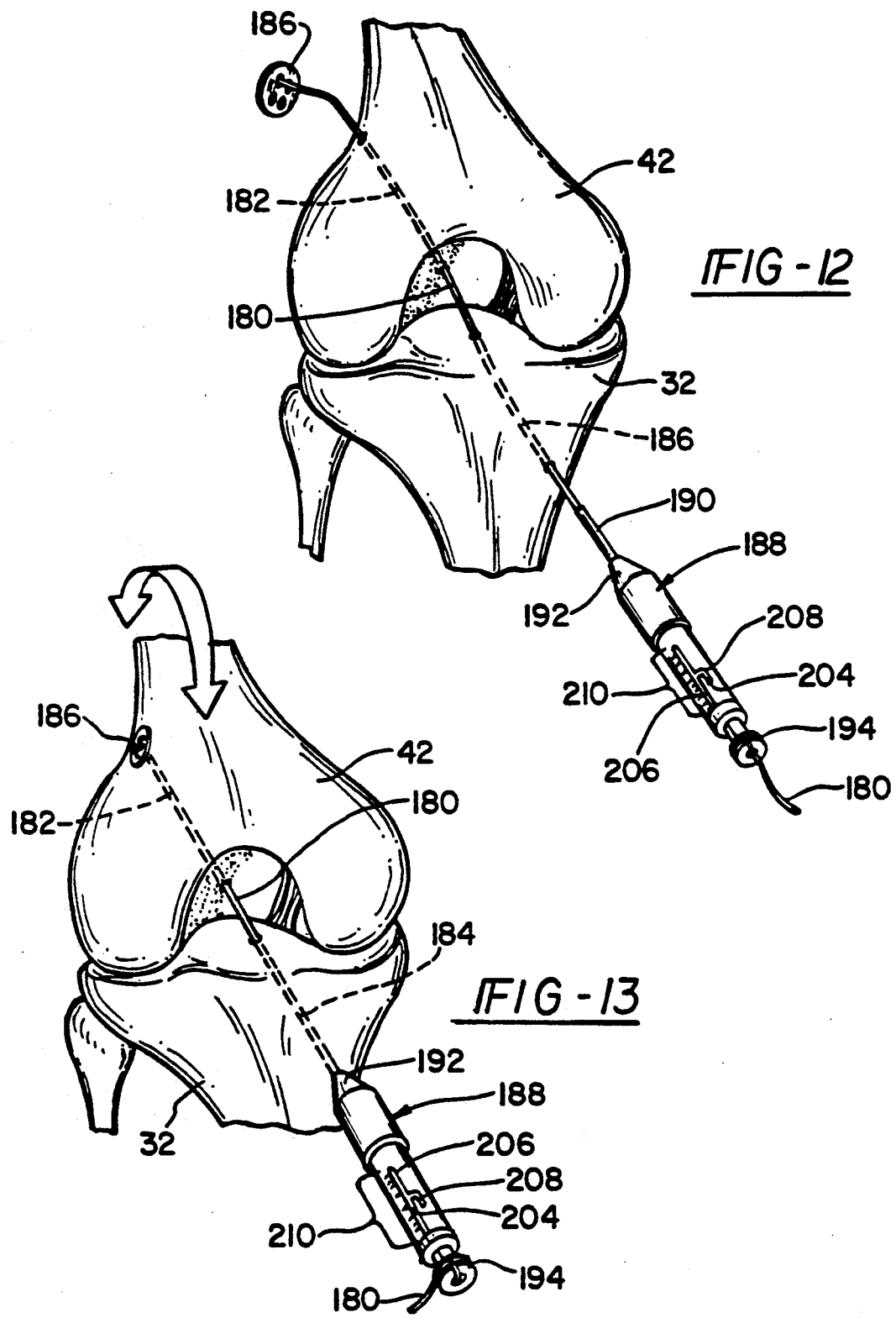

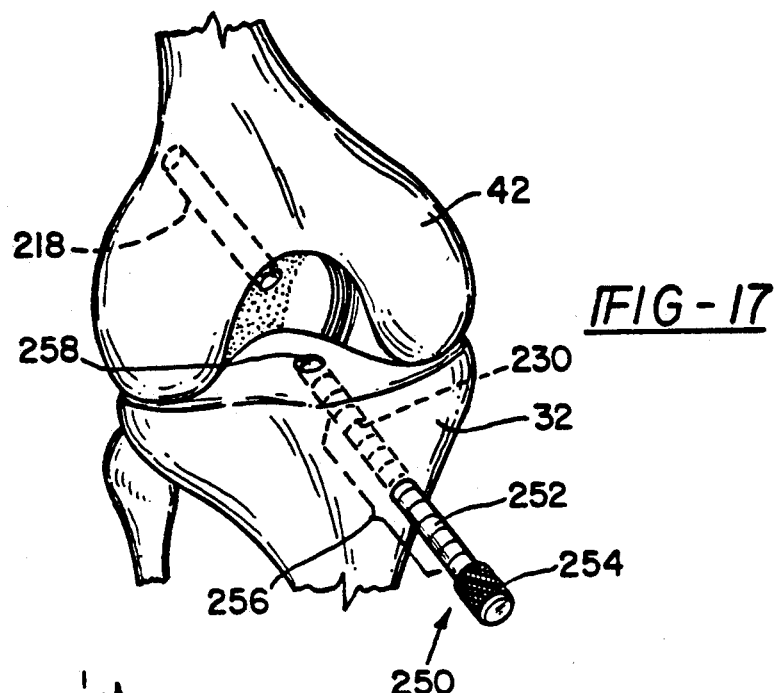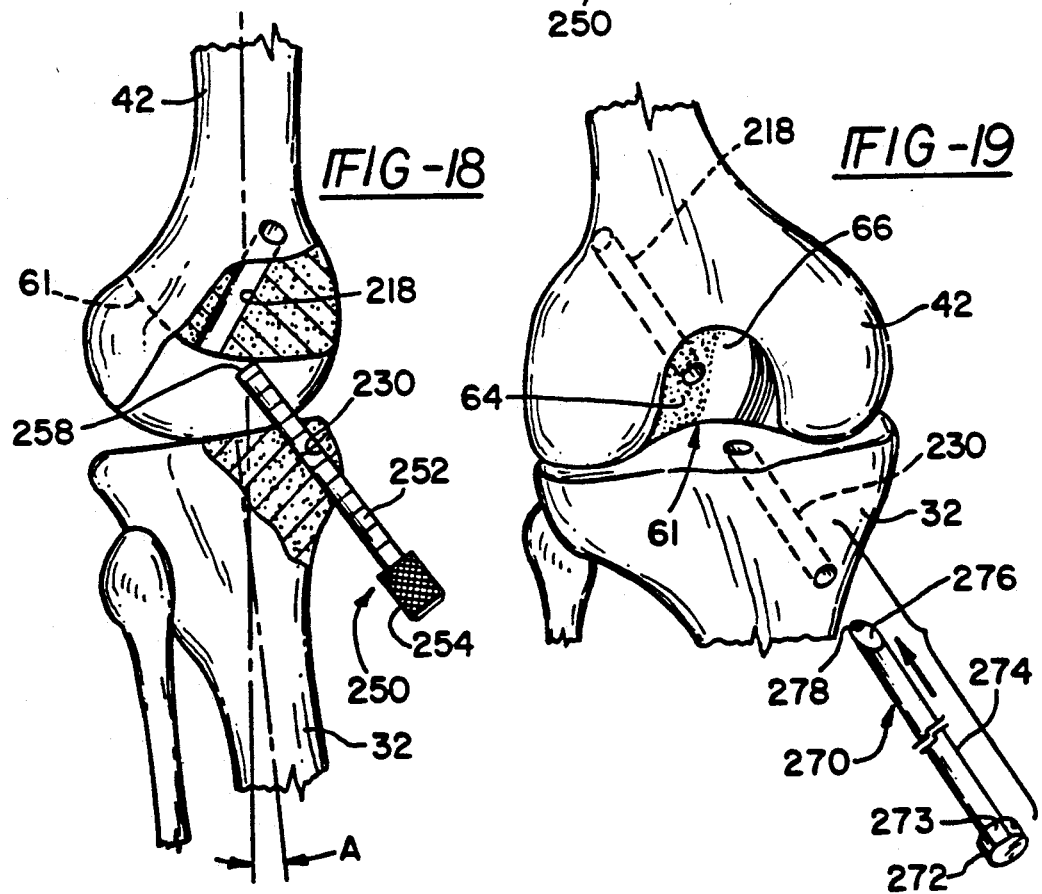

METHOD AND INSTRUMENTS FOR ACL RECONSTRUCTION

This is a continuation of U.S. patent application Ser. No. 552,815, filed Jul. 16, 1990. Entitled: Method & Instruments For ACL Reconstruction, now abandoned.

TECHNICAL FIELD

The present invention relates to an improved method for reconstruction of a torn anterior cruciate ligament using endoscopic techniques, as well as new and improved instruments for use with the method.

BACKGROUND OF THE INVENTION

Most people today are involved in a sport or some other type of physical activity. Some of these activities involve a low risk chance of injury, such as walking and swimming, while others involve a high risk chance of injury, such as football and skiing.

Damaged ligaments, cartilage and tendons in joints are not an uncommon occurrence, particularly in some of these high risk activities and sports. One of the joints which requires particular skill and presents particular difficulties in repairing is the knee joint.

Numerous improvements in repairing damage to knee joints have been made over the years, and some of the major advances involve the use of endoscopic techniques and arthroscopic procedures. Arthroscopic surgery is particularly useful in excising or repairing damaged knee cartilage.

Endoscopic techniques have also been developed for use in repair and reconstruction of damaged anterior cruciate ligaments (ACL) and posterior cruciate ligaments (PCL). When the ACL in particular has ruptured and is nonrepairable, it is usually replaced in young adults and the knee reconstructed through use of grafts (biological or synthetic). Some known methods and techniques which have been used to repair and replace ACL ruptures with grafts are discussed, for example, in Moore U.S. Pat. No. 4,773,417, Goble U.S. Pat. No. 4,772,286 and an article by Goble entitled "FLUOROARTHROSCOPIC ALLOGRAFT ANTERIOR CRUCIATE RECONSTRUCTION", Techniques Orthop. 1988 2(4):65-73.

The function of the real cruciate ligaments is complicated. The ACL and PCL are three-dimensional structures with broad attachments and a continuum of fibers. These fibers are of different lengths, have different attachment sites, and are under different tensions. Although many current substitutes for cruciate ligaments have not duplicated the complex orientation and operation of normal ACLs, they operate the best and mimic the normal ACL operation the best when they are placed isometrically. "Isometrically" positioned means that the length of the substitute ligament will not change during angular movement of the tibia relative to the femur; the distance between the affixed ends of the ligament remains a constant. Isometric placement maximizes the number of fibers that can be taut throughout the range of motion of the knee and allows for early knee motion without generating high ligament strains.

Correct isometric positioning of the ACL graft is an important factor for a successful operation; isometrically placed grafts provide the most stable knees. Correct isometric placement reproduces corresponding femoral and tibial anatomic attachment sites and will allow an ACL graft to mimic the normal ACL. Non-isometric graft placement can result in plastic deformation of the ACL substitute, postoperative laxity, abnormal kinematics, or failure of fixation.

The importance of accurate placement of the graft tunnels and ACL substitute is shown by the fact that graft placements sometimes only several millimeters apart produce significantly different strains in the cruciate substitute. A placement of the ACL origin or insertion which is too anteriorly placed in the knee joint results in a ligament that is taut in flexion, but lax in extension. Posterior placement causes the ligament to be taut in extension, but lax in flexion. Only isometric tunnel placement provides stability throughout the range of motion.

The preparation of the intercondylar notch is also important as is the proper positioning and placement of the femoral and tibial tunnels. Accurate and sufficient notchplasty prevents impingement of the graft which could cause failure or significant complications. Often today the amount and degree of notchplasty is determined during an operation by "feel" or experience. This frequently results in more of the bone in the notch being removed than is necessary, or in less of the bone being removed than is required necessitating later correction in the operation.

It is an object of the present invention to provide an improved method using endoscopic/arthroscopic techniques for reconstruction of ACLs. It is a further object to provide isometric placements of ACL substitutes, and isometric placements which are objectively accurate and reproducible.

It is also an object of the invention to insure against impingement of the ACL substitute/graft in the joint. It is another object of the invention to provide a system for accurately determining whether notchplasty needs to be performed in the intercondylar notch to prevent impingement, and then performing the necessary notchplasty.

It is still a further object of the invention to provide an ACL replacement which is minimally invasive in order to minimize trauma and facilitate faster patient healing and rehabilitation. It is another object to provide a method of ACL reconstruction which preferably uses biological grafts from the patient.

Further objects of the invention include development and use of improved instruments for ACL operations which help assure accurate and sufficient notchplasty of the intercondylar notch, and provide an improved method for ACL reconstruction.

BRIEF DESCRIPTION OF THE DRAWINGS

FIGS. 12 and 13 depict use of a tensiometer in isometrically determining the positioning of the osseous tunnels;

FIGS. 17 and 18 illustrate use of the unique sizer member in accordance with the present invention to determine possible ACL graft impingement in the intercondyle notch;

FIGS. 19 and 20 illustrate use of the unique gouge instrument to mark the location of the roofplasty necessary to eliminate possible ACL graft impingement.

DISCLOSURE OF INVENTION

Figure 1:
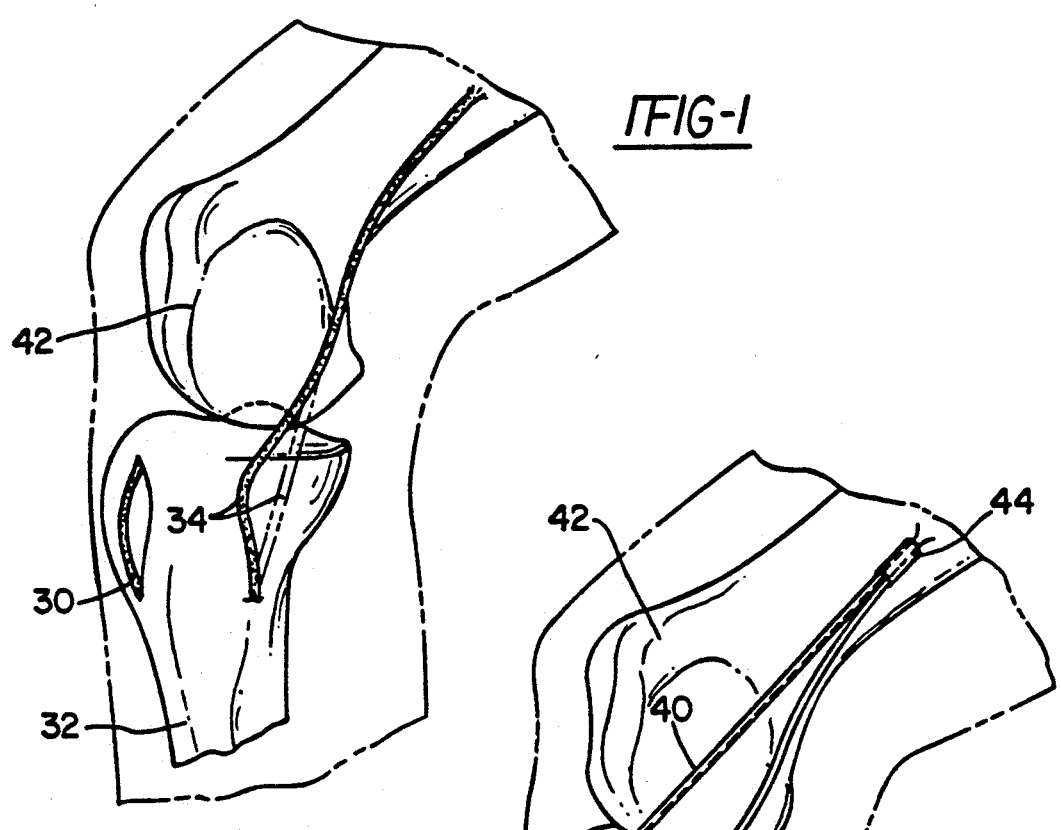
FIGS. 1 and 2 are schematic perspective views of the harvesting of the tendons for use as an ACL replacement in accordance with the present invention.

The above and other objects of the invention are met by the inventive method of ACL reconstruction and instrumentation which are disclosed and claimed in this application.

For the improved method, the knee joint is examined to confirm the rupture. The patient is anesthetized and the surgical site prepped and draped. The gracilis and semitendinosus tendons are harvested from the patient for use as the graft (or another type of ACL substitute is obtained). The graft is prepared for later implantation. Sutures are stitched at the free ends of the tendons for use in grasping and handling them and the tendons are double-looped forming a composite graft. The size of the graft is measured in order to select the proper drill/reamer size for the osseous tunnels.

The knee is examined by arthroscopic procedures and any observed minor defects or irregularities are taken care of. The lateral wall of the intercondylar notch is debrided and sculptured (i.e. "wallplasty"). Both manual and powered instruments can be used for this purpose. The torn ACL stump is removed from the intercondylar notch and the joint is cleaned.

The femoral attachment site for the ACL graft is determined visually and marked with a small recess by a curette. The femoral lateral cortex is exposed and a rear entry drill guide is utilized to drill a small hole through the femur to the recess.

A unique transverse drill guide is used to position and place a locator pin transversely through the femur. The transverse drill guide has an elongated slide bar, a bent wire aimer with a curved tip, a drill sleeve and a drill sleeve positioning member. The aimer has a groove which is adapted to nest with the intercondylar notch in order to accurately position it in place. Once the aimer and attached slide bar are positioned in place, the positioning member slides on the slide bar and positions the drill sleeve in the proper position. The transverse locator pin is drilled through the drill sleeve and passes through the intercondylar notch adjacent the curved tip of the aimer.

The transverse locator pin is used to position a unique anterior tibial drill guide which in-turn is used to drill a small hole through the tibia intercondylar roof with the knee in hyperextension. The anterior tibial drill guide utilizes the same drill sleeve positioning member as the transverse drill guide and also includes an elongated slide bar and bent wire hook. The curved tip of the bent wire hook is hooked over the femoral transverse locator pin and the top of the bent wire hook is positioned against the roof of the intercondylar notch. A small hole is drilled in the tibia through a drill sleeve situated in the positioning member on the slide bar.

The small holes in the femur and tibia preferably are then checked isometrically to determine if they are the proper sites for the osseous tunnels for the ACL graft. A suture passed through the two holes is secured to a button on the lateral femoral cortex and passed through and secured to a tensiometer on the tibia. The tensiometer is unlocked and readings are taken during movement of the knee.

If the proposed site is isometric, then the femoral and tibial tunnels are drilled. Guide pins are positioned in the two tunnels and the tunnels are drilled using cannulated drills or reamers placed over the pins. The inner edges of the tunnels are smoothed and chamfered.

The possible impingement of the roof of the intercondylar notch on the substitute ACL graft is then checked. A calibrated sizer is passed through the tibial tunnel and any impingement noted. If any impingement is determined, it is marked with a unique gouge instrument and a roofplasty is performed. The sizer is reused and the knee analyzed again until all of the impingement has been eliminated.

The substitute ACL graft is then passed through the osseous tunnels and secured in place. The double-looped end of the graft is affixed to the lateral femoral cortex by a cancellous screw. Once the graft is pulled tightly into position and minimal movement of the graft during rotation of the knee is observed, the graft is affixed to the tibia by bone staples.

After the graft is fully secured in place and examined, the wounds around the knee are closed and dressed. A leg brace is installed and appropriate postoperative care is followed.

BEST MODES FOR CARRYING OUT THE INVENTION

For a knee reconstruction involving an unrepairable or torn anterior cruciate ligament (ACL), the procedure begins with a general anesthesia being administered to the patient. The patient is positioned supine on the operating table. A well-padded tourniquet is placed proximal on the thigh of the affected leg, although the tourniquet is not inflated until later. An arthroscopic leg holder is placed around the tourniquet. The table is inclined (e.g. 15° of trendelenburg) and adjusted in height (e.g. waist level) according to the desires of the surgeon. The other leg is secured to the foot of the table. A Mayo stand is placed over the leg holder and positioned to permit access to the lateral thigh.

The surgical site is prepped and draped with a sterile seal. Standard arthroscopic draping is performed covering the Mayo stand. The light cord, camera, motorized instruments, and inflow, outflow and suction tubing are wrapped and secured to the drape on the Mayo stand. The irrigation stand is set up and positioned.

The joint of the affected leg is examined physically to confirm a rupture of the ACL and to determine the amount and degree of movement (joint looseness).

The graft harvesting step in the procedure depends on the type of ACL substitute that is to be utilized. In accordance with the present invention, preferably the gracilis and semitendinosus tendons are harvested from the patient and used as the ACL substitute. These provide a graft which is stronger in the joint (over twice the strength of the original ACL) and has less postoperative morbidity. However, it is also possible in accordance with the present invention to use other known ACL substitutes, such as patellar tendons, autogenous tendons, frozen and lyophilized tendon allografts, or some of the various known synthetic materials. Although the harvesting and preparation techniques may be different or eliminated altogether with other ACL substitutes, their installation and attachment to the femur and tibia are preferably the same as that described below relative to placement and attachment of harvested semitendinosus and gracilis tendons.

A tibial incision is used for harvesting the semitendinosus and gracilis tendons as well as for use as the site for making the tibial tunnel. The anterior tibial crest and the posteromedial margin of the tibia are outlined with a marking pen. The incision overlies a line which bisects that outline. A longitudinal incision about 4 cm in length is centered at a point about three finger widths distal to the anteromedial joint line over the bisecting line.

The incision is made with a No. 15-blade through the skin and subcutaneous tissue. Electrocautery is used for hemostasis. Subcutaneous fat is elevated off the sartorius expansion from the anteromedial tibial crest to the posteromedial tibial edge. A rake is used to medially displace the medial edge of the incision and the gracilis tendon is palpated.

An incision 30 is made in the tibia 32 parallel and inferior to the gracilis tendon by cutting through the sartorius expansion (see FIG. 1). The incision is angled 90° proximally along the medial tibial crest of the tibia 32 for approximately 15 mm. With the knee at 90° the gracilis tendon 34 is isolated manually and a penrose drain or equivalent device is passed around it to maintain tension on it. The tendon is detached carefully from the tibia preserving maximal length.

Figure 2:
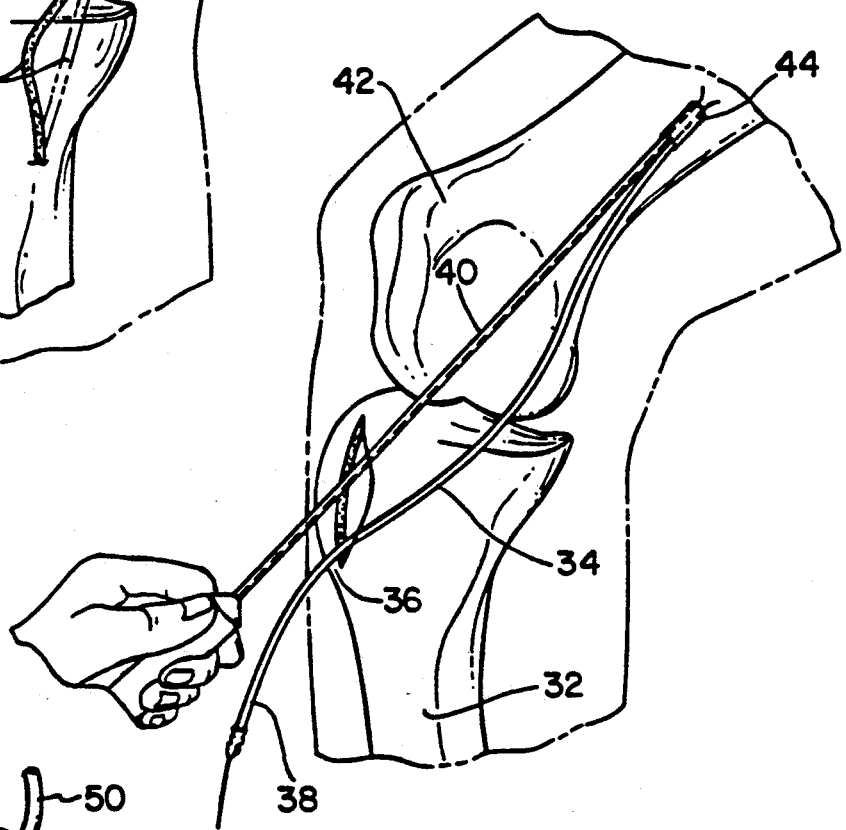

As shown in FIG. 2, the detached end 36 of the tendon 34 is prepared for grasping by installation of sutures 38 using a No. 1 Ethibond suture and a tendon needle. A number of "whip" stitches are weaved about 4 cm up along each side of the detached tendon.

The tendon 34 is cut free from attachments along its length by metzenbaum scissors. The sutures 38 are tugged gently until the tendon can be seen to move freely.

The gracilis tendon 34 is removed by a tendon stripper 40, such as the closed end or slotted end tendon strippers marketed by Acufex Microsurgical, Inc., Norwood, Mass. After the loose end of the tendon is positioned in or threaded through the stripper instrument 40, the tendon is grasped and held in tension manually by the sutures 38. The stripper 40 is slowly advanced up the length of the tendon until the tendon is completely separated from the femur 42 and delivered. The stripper circumferentially divides the tendon using its sharp leading edge 44. With this procedure, the length of the harvested tendon is maximized. The length of the tendon should be sufficient so it can be "double-looped" when used as the ACL replacement graft.

Precisely the same steps and procedures are used to isolate, detach and harvest the semitendinosus tendon. The length of the semitendinous should also be maximized so it can be "double-looped" into a strong graft.

Figure 3:
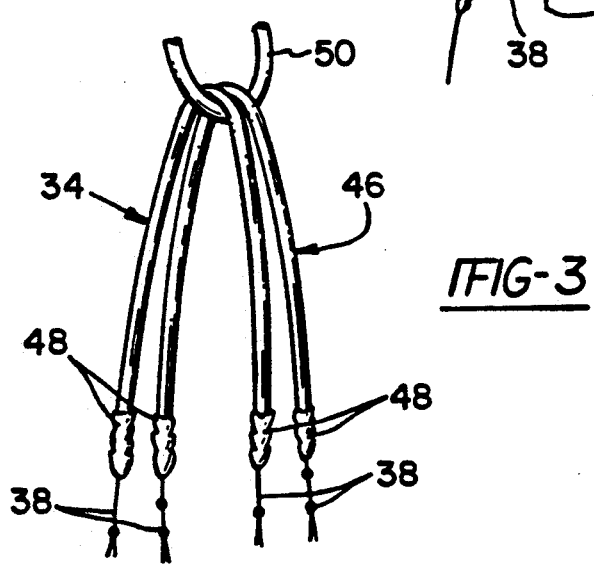
FIG. 3 illustrates harvested tendons prepared for use as an ACL graft in accordance with the present invention.

After the two grafts are harvested, they are prepared and sized. (The preparation and sizing steps can be performed by a surgical assistant while the surgeon continues with the rest of the ACL replacement procedure.) Any remaining muscle fibers are removed from the grafts and whip stitches are made with No. 1 Ethibond sutures approximately 4 cm from the proximal end of each tendon. FIG. 3 shows a double looped gracilis tendon 34 and a double looped semitendinous tendon 46. The sutures 38 are attached to the free ends of the tendons with the whip stitches 48. For identification of the tendons and associated sutures, the sutures on each tendon can be tied with a different number of knots (e.g. two knots in the semitendinosus sutures and one knot in the gracilis sutures).

The pair of double looped tendons 34 and 46 are bundled together to form a composite graft 52. An umbilical tape 50 is looped around the midpoint of both tendons and is later used to pass the tendons through the osseous tunnels, as explained below.

In order to determine the proper size of the osseous tunnels, the bundled graft 52 (together with the umbilical tape and sutures) are passed through conventional incremental graft sizing tubes. An average graft should fit snugly into an 8 mm sizer which provides a 50 mm$^2$ cross-section identical in size to an average ACL. The proper diameter for reaming is obtained when the graft 52 firmly fits in the sizer; it should not be loose.

If another type of ACL graft is to be utilized instead of the gracilis/semitendinous tendon graft 52, it should be prepared in a similar manner. Sutures should be attached to the ends of the graft to aid in grasping, manipulating and securing the graft in place. Incremental sizing tubes are used to size the graft and select the appropriate drills for forming the tunnel. Installation and attachment of the graft to the femur and tibia are essentially the same as that which will be described below relative to placement and attachment of graft 52, although other conventional or standard procedures may be utilized.

The prepared knee is now examined by arthroscopic procedures. Standard anterolateral and anteromedial portals are made for the diagnostic arthroscopy. Proper portal placement is important. Preferably, the lateral portal is made at a location one-third the width of the patella ligament medial to the lateral margin and positioned vertically just inferior to the inferior patella tip. The medial portal is made vertically, just inferior to the inferior patella tip and adjacent to the medial border of the patella ligament. The two portals should be located at the same level.

The fat pad is pushed away from the area by distension of the knee and diagnostic arthroscopy is performed. Any observed meniscal damage, osteophyte and unstable joint surfaces are appropriately treated by standard arthroscopic techniques and the status of the cruciate ligaments is confirmed.

Debriding and sculpting of the lateral side of the intercondylar notch 61 is then performed (still without inflation of the tourniquet). This is commonly called wallplasty. Preferably a 5.5 mm full-radius synovial resector is used through the medial portal. A conservative trimming of the fat pad is accomplished, starting laterally and ending medially. These steps allow better observation of the notch.

Figure 4:
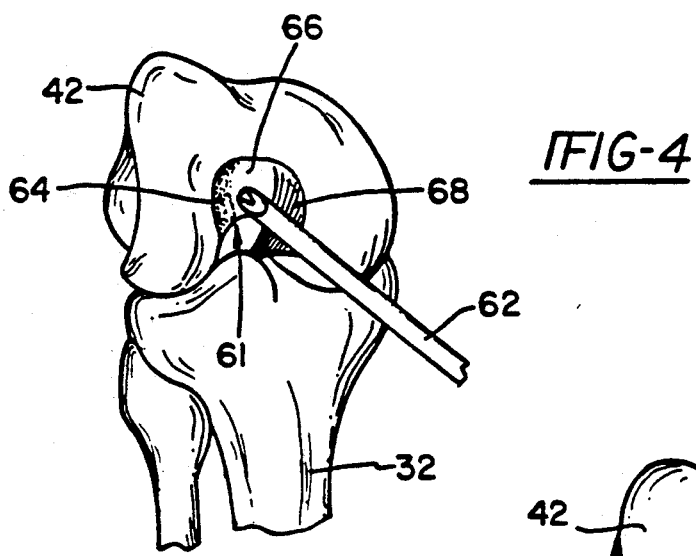
FIG. 4 is a schematic perspective view of the wallplasty procedural step for ACL reconstruction in accordance with the present invention.

The wallplasty is performed using a notchplasty gouge 62, as shown in FIG. 4, to remove 3-5 mm of the lateral condylar wall 64. No bone is removed from the intercondylar roof 66 at this point.

An up-angled, curved and uterine curette is used through the medial portal to remove the origin (and stump) of the ACL from the intercondylar roof and the wall of the lateral femoral condyle. The retained synovial and cruciate remnants are cleaned and vacuumed with a full-radius resector. (Care should be taken to protect the PCL 68 and avoid injury to it and its synovium.) Preparation is complete when a probe can be used to palpate the posterior ridge of the intercondylar roof 66 with clear, unobstructed visualization.

The site for placement of the femoral guide pin is then selected. This is the first step in determining the location of the osseous tunnels in the femur and tibia. The placement of these tunnels is important since they must enter the joint at the proper anatomic attachment points (where the original ACL was attached).

Figure 5:
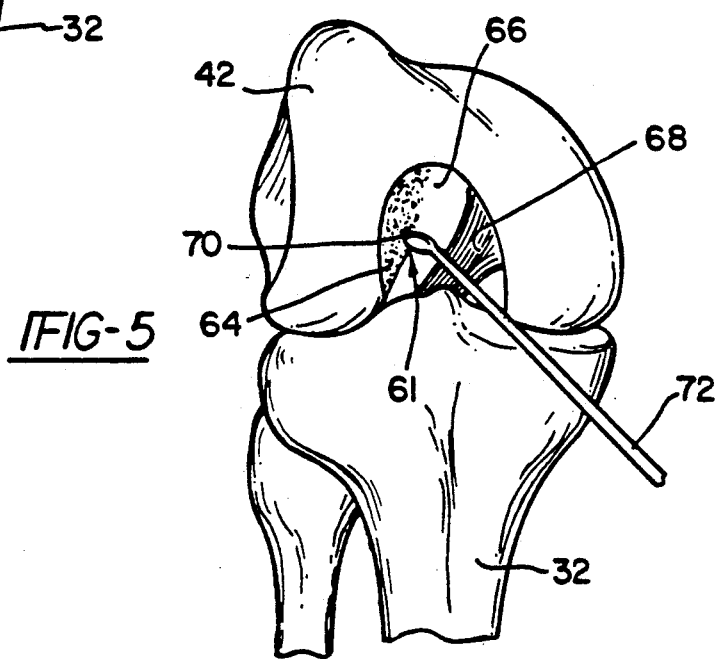
FIG. 5 illustrates the marking of the femoral attachment site with a curette.

The reference point for determining the location of the intra articular entrance point of the femoral guide pin is the posterior arch of the intercondylar notch. A nerve-hook probe is manipulated through the medial portal until the angled tip is oriented at the surgeon's discretion relative to the floor and camera projection (preferably perpendicular). The tip of the probe is positioned to cradle the posterior edge of the intercondylar notch in the over-the-roof position. The tip is then slid forward about 5 mm from the posterior edge and rotated either to the 11:00 position (for a right knee) or the 1:00 position (for a left knee). This position is then marked by boring a small recess 70 with an angled cervical curette 72. This is shown in FIG. 5. The pin site selection is confirmed by palpating with the probe.

The arthroscopic instruments and fluid are removed from the joint. The leg is exsanguinated and the tourniquet is now inflated. Next, the lateral femur is exposed.

Figure 6:
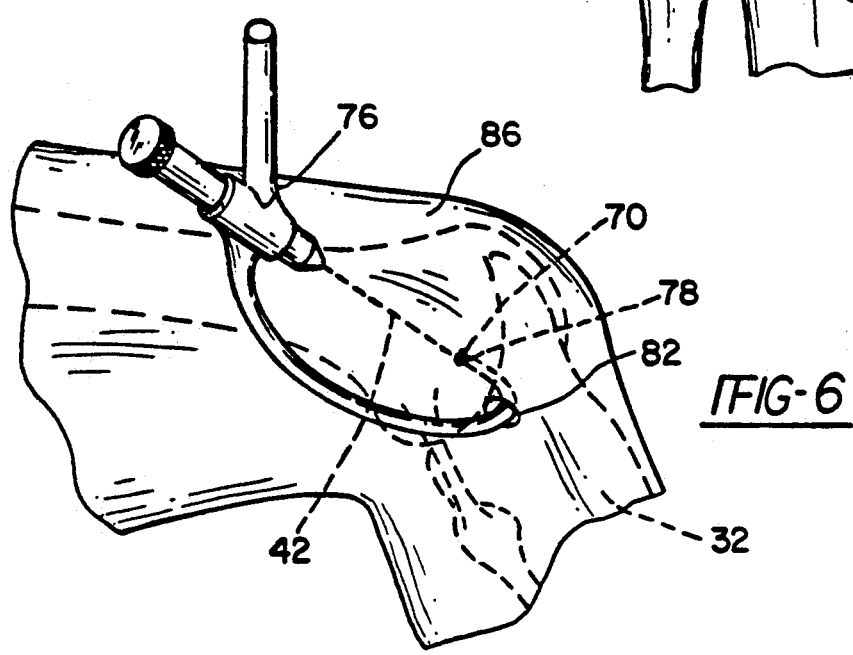
FIG. 6 illustrates the marking of the location of the lateral femoral incision.

The site for the incision on the lateral femur is then determined. This can be determined visually from experience or teaching, or a guide instrument can be utilized. The front entry guide system by Acufex Microsurgical, Inc. can be used, for example, as shown in FIG. 6. The guide 76 is brought into the joint through the lateral portal 82 and the tip 78 is centered in the small recess or hole 70 marked previously with the curette. The remaining portion of the guide 76 is brought to rest on the skin 86 overlying the anterolateral femur, just proximal to the metaphyseal flair.

An incision about 4 cm in length is made just proximal to the medial epicondyle and parallel to the long axis of the femur. If the incision site is too anterior the guide 76 will not rest on the lateral aspect of the skin. If it is too posterior, the guide will hang up on the anterior skin.

Figure 7:
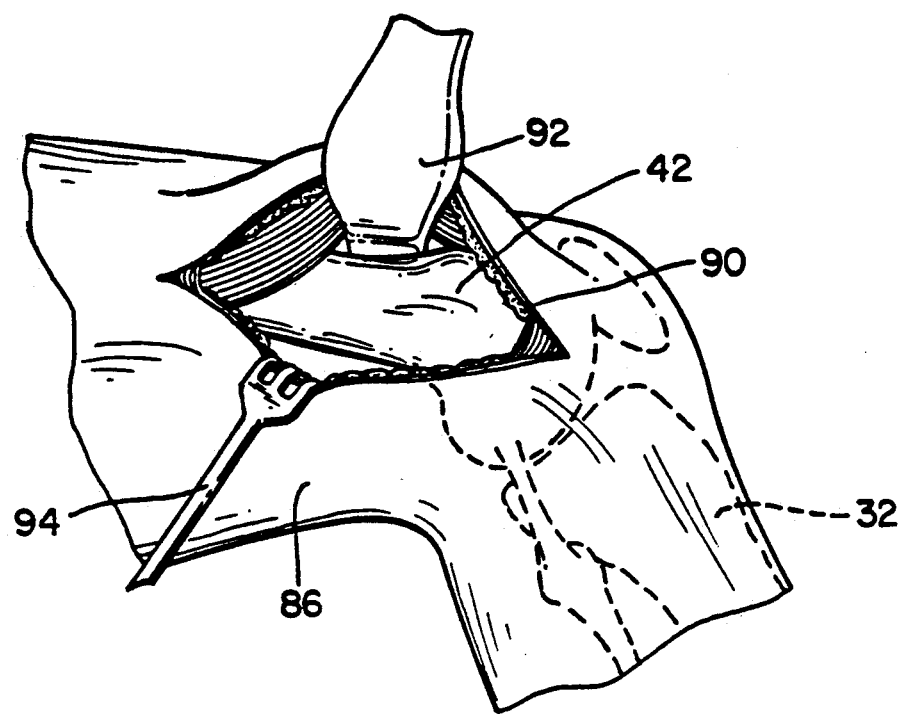
FIG. 7 illustrates the lateral femoral incision procedure.

A skin incision 90 is made through the IT-band and the subcutaneous fat is swept off posteriorly. This is shown in FIG. 7. The IT-band is incised and the incision extended distally approximately 10 cm up the thigh. A lateral retractor 92 is placed between the periosteum and muscle mass. The superiorlateral geniculate vessels are identified and cauterized. The periosteum is incised longitudinally and the lateral retractor 94 is replaced deep to it on the anterior femur and stabilized.

Figure 8:
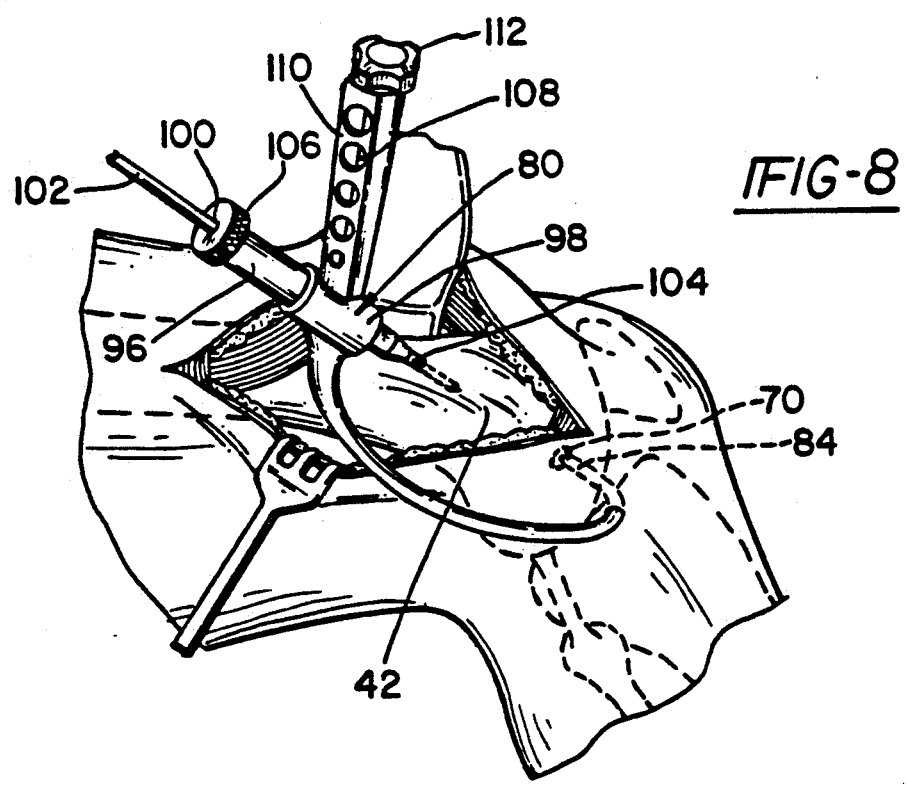
FIG. 8 shows drilling and positioning of the femoral guide pin with the rear entry guide.

As shown in FIG. 8, a rear entry drill guide 80, such as the Acufex Microsurgical rear entry drill guide system, is then used to drill the hole for the femoral guide pin. The drill guide 80 is positioned and placed in the joint by a gaff. The tip 84 of the guide is secured in the recess 70. A "bullet" (drill sleeve) 96 is placed in the drill sleeve collar 98 of the drill guide 80. The drill sleeve 96 is hollow having a passageway 100 for placement therethrough of a sharp pointed wire-type drill 102, such as a K-wire. The front end 104 of the bullet 96 has a sharp tri-point and the rear end 106 has a knob for ease of grasping and manipulation.

Once the tri-point bullet 96 is positioned in the tubular collar 98 with the tip against the appropriate position on the lateral cortex of the femur 42, it is locked in place by a long threaded rod 108 positioned in handle 110 of the drill guide 80 and operated by turn knob 112. The rod 108 is threaded through a threaded opening (not shown) in the collar 98 and makes contact with the bullet 96. When the rod is rotated by the knob, it forces the bullet in a fixed engaging relationship with the inner wall of the collar 98 holding the two members firmly locked together.

Once the drill guide 80 and bullet 96 are firmly set in place, the wire drill (K-wire) 102 is passed through the bullet and drilled into and through the femur using a conventional surgical motorized drilling instrument. Due to the shape of the drill guide 80, the drill 102 placed in the bullet 96 will always hit the tip 84 of the guide wherever it is placed. Preferably a 2 mm wire drill is used.

After accurate positioning and placement is confirmed arthroscopically, the wire drill is drilled into and out of the passageway several times (preferably 8-10 times) to make a uniform tunnel. The bullet 96 is then released from the collar 98 and removed from the guide 80, leaving the K-wire (or substituted guide pin) in place. The drill guide 80 is also removed.

If desired, a 6 mm cannulated reamer is used to broach the outer femoral cortex to outline the pin tract so that the wire drill or guide pin can be removed. A 1-PDS suture, loaded on an 18-gauge spinal needle, is then passed into the joint through the drilled hole.

It is also possible in accordance with the present invention, to make the femoral tunnel in another manner. For example, the femoral tunnel could be made using Acufex's endoscopic system or front entry guide system. Other conventional procedures can also be utilized.

Figure 10:
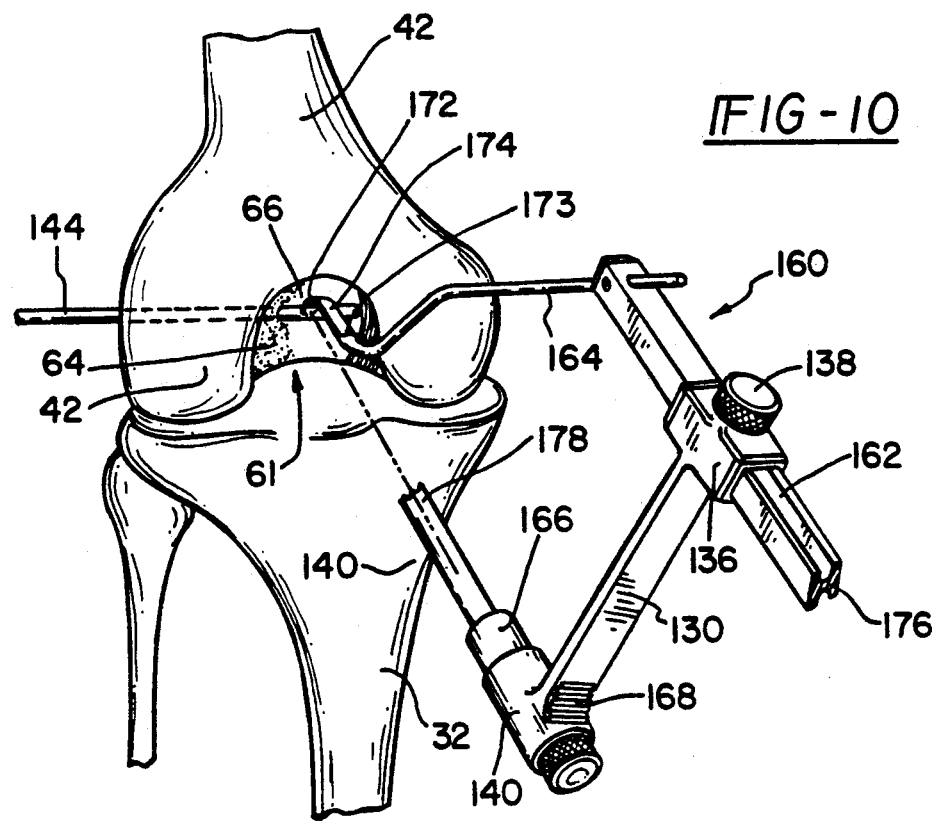
FIG. 10 and 11 illustrate placement and use of the anterior tibial drill guide to position and place the tibial guide pin.
Figure 11:
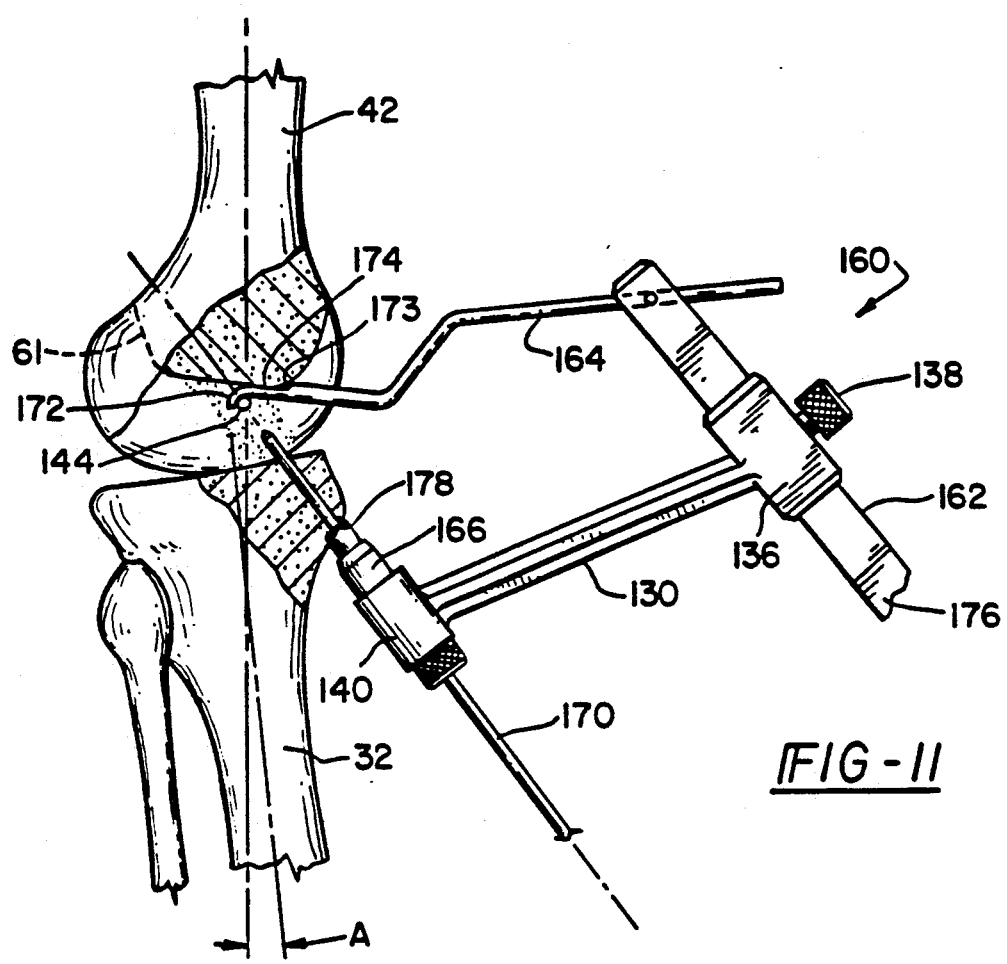

Once the positioning of the femoral guide pin has been established indicating the prospective position of the femoral tunnel for the ACL graft, the position for the guide pin for the proposed tibial tunnel is determined. A set of unique drill guides of the shape and structure shown in FIGS. 9-11 are used to position and place the tibial guide pin.

Figure 9:
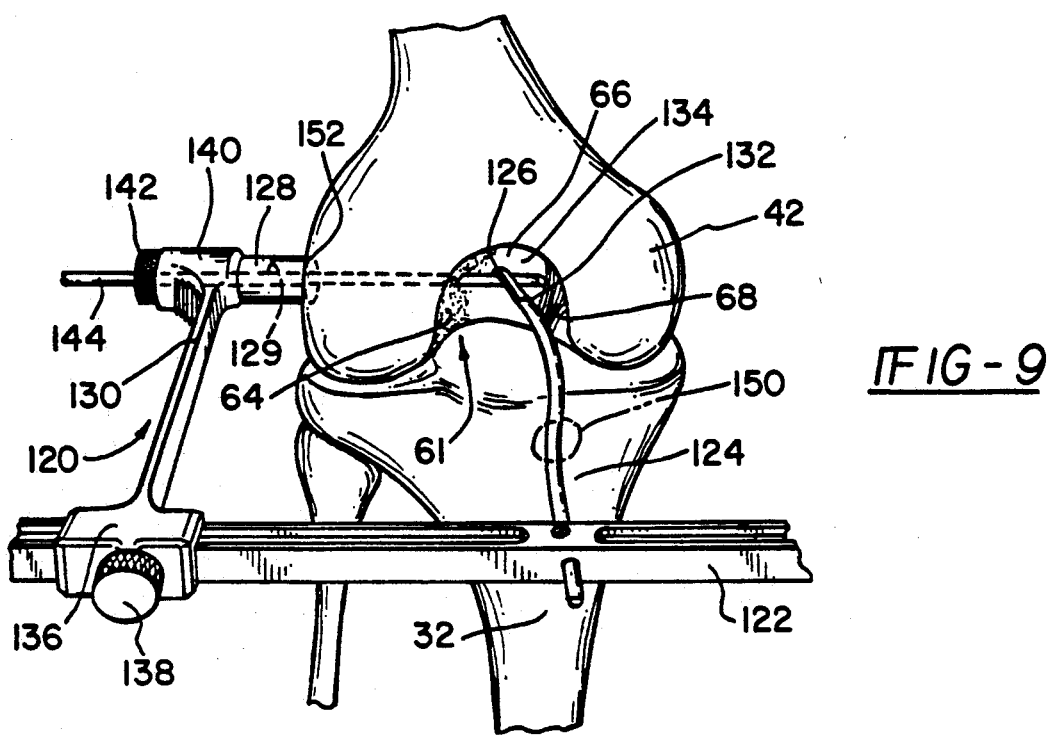
FIG. 9 illustrates placement and use of the transverse drill guide to place the transverse femoral locator guide pin.

First a transverse drill guide 120 is utilized (FIG. 9). The guide 120 has an elongated slide bar 122, a bent wire aimer 124 with a curved tip 126, a wire drill sleeve 128, and a drill sleeve positioning member 130. The aimer 124 has a notch 132 defining a convex flattened top surface and is adapted to nest in and mate with the cartilaginous surface 134 of the intercondylar notch 61. The tip 126 is curved about 90°.

The positioning member 130 has a base 136 which has a channel in it to allow the member 130 to fit over and slide along the slide bar 122. A threaded set screw 138 with an enlarged head for manual grasping and tightening is used to hold the member 130 in the desired position on the slide bar. The drill sleeve 128 is received in a collar 140. The collar 140 has internal threads which mate with a series of external threads on the outer surface of the sleeve 128 so that the sleeve can be secured in place relative to the collar. The sleeve 128 has an enlarged end 142 which is used to manually turn and tighten the sleeve in the collar. The sleeve 128 has a central passageway 129 through it for holding and positioning a wire-type drill 144.

In use, the transverse tibial drill guide 120 (without the positioning member 130 thereon) is first put into position. The bent wire aimer 124 is brought through the anteromedial portal 150 and aligned so that the notch 132 is positioned against the cartilagenous surface 134 of the anterior edge of the intercondylar notch. (If the position of the portal 150 is not appropriate, then another portal, such as a central patellar portal, can be made and utilized.) More particularly, the aimer is placed against the roof 66 of the intercondylar notch 61 with the knee at about 30°-45° flexion. The notch or "step-off" 132 is placed against the anterior aspect of the notch. The guide 120 is held firmly in this position approximately perpendicular to the longitudinal axis of the tibia and femur.

The drill sleeve 128 is tightly threaded into the collar 140 of the positioning member 130 and the positioning member 130 in turn is placed on the slide bar 122. The member 130 is moved along the bar 122 toward the aimer 124 until the end 152 of the drill sleeve 128 abuts the lateral external surface of the thigh.

A wire drill 144, which preferably is a 0.062 diameter K-wire, is positioned in the drill sleeve 128 and drilled by any conventional motorized drilling mechanism through the lateral femur, (as shown in FIG. 9). The wire drill passes from lateral to medial in the femur 42 to outline a window to contain the tip of the anterior tibial drill guide 160 (as shown in FIGS. 10 and 11) between the intercondylar roof 66, the lateral edge of the PCL 68, and the medial wall of the lateral femoral condyle 64. The wire drill is advanced just to or into the PCL and not into the medial femur.

Once the wire drill 144 is installed in place in the femur 42, the transverse drill guide 120 is removed. The positioning member 130 is loosened and removed from the slide bar 122, and the aimer 124 is removed from the medial portal. Since the wire drill 144 (or substitute guide pin) is left in position in the femur, it is necessary to rotate the aimer in order to remove it from the joint. If there is difficulty in removing the hook of the transverse guide from the transverse pin, the pin can be backed away from the PCL until the hook is removed and then readvanced.

Once in place the wire drill (K-wire) 144 becomes a transverse locator pin (although it is also possible in accordance with the present invention to replace the wire-type drill with a guide pin). The drill or pin is positioned in the joint a few millimeters distal to the roof 66 and enters the medial side of the notch approximately where the PCL is attached.

The anterior tibial drill guide 160 is then put into position through the anteromedial portal. This is shown in FIGS. 10 and 11. This drill guide 160 has an elongated slide bar 162 and a bent wire hook 164. The positioning member 130 which is used on the transverse drill guide 120 to position and place the drill 144 acting as the transverse guide pin 144 is also used with the anterior tibial drill guide 160.

The base 136 of the positioning member 130 fits over and slides along the slide bar 162. The screw 138 is used to hold the member 130 in place on the bar once it is put in its proper position. A tri-point "bullet" drill sleeve 166 is positioned in the collar 140. A series of threads on the outer surface of the bullet 166 mate with the threads on the inner surface of the collar 140 and are used to tightly hold the bullet in position within the sleeve 140. The bullet 166 has a central passageway 168 through it for holding and positioning a wire drill (K-wire) 170.

With the knee slowly being extended, the hook 164 is brought into the joint through the anteromedial portal. The hook is rotated and the curved tip 172 of the hook 164 is positioned within the "window" over the drill 144 acting as the transverse guide pin 144. This sets the position for accurately drilling and setting of the tibial guide pin in the proper orientation and position. A curved notch 174 defining a convexly curved and flattened upper surface of the hook 164 is pushed posteriorly until it is positioned against the anterior aspect of the intercondylar notch 61 and the hook is tightly held in this position. For this procedure, the knee is deflated by removal of irrigation fluid and the knee is placed in maximum hyperextension, usually 5°-10°, as shown in FIG. 11.

The anterior tibial drill guide 160 is raised or lifted until the flat upper surface 173 of the hook 164 is substantially perpendicular to the long axis of the femur 42. The concave lower surface of hook 164 is shaped to receive and nest with the transverse pin 144. Resistance will be felt as the guide attempts to angulate the drill 144 acting as the transverse pin.

The bullet drill sleeve 166 is positioned in the member 130 and tightly screwed into place. The member 130 is then slid over the end 176 of the slide bar 162 until the tri-point end 178 of the bullet abuts against the cortex of the tibia 32. With the hook 164 held tightly against the intercondylar roof and the drill guide 160 held perpendicular to the longitudinal axis of the femur, the bullet drill sleeve 166 is set in the proper position. The wire drill 170 is placed in the bullet 166 and drilled through the tibia into the joint by any conventional motorized drilling mechanism.

The wire drill (K-wire) 170 is drilled into and out of the drilled hole several times to create a uniform tunnel. The positioning member 130 and drill guide 160 are removed. It is also possible to remove the drill 144 acting as the transverse guide pin at this point since it has fu purpose, and substitute a guide pin for the wire drill 170 if desired (or remove it entirely).

The location of the original ACL fibers on the tibial joint surface are used as a landmark to check on the placement of the tibial guide pin. The pin should protrude from the tibia into the joint at the original ACL site. When the knee is at maximum passive hyperextension, the pin should be parallel and 4-5 mm posterior to the intercondylar roof. If the drill 170 is too lateral or medial, then refinement of the guide pin alignment can be accomplished with a 3 or 5 mm hole changer.

The femoral drill hole formed in the manner described earlier and the tibial drill hole formed in the manner described immediately above should be in alignment and substantially parallel to each other. Once they are formed, their positions are checked to determine if they are properly placed isometrically.

In order to assess isometry of the two drill holes for use as the positioning for the osseous tunnels, a suture is first passed through them. This is shown in FIGS. 12 and 13. The suture 180 loaded on the spinal needle in the femoral drill hole 182 is grasped by a grabber in the joint and pulled through the tibial drill hole 184. A 2 mm suture passer also is utilized.

A sterile button 186 is tied on the femoral side of the suture and the stitch is pulled through the joint until the button lies flush on the femoral cortex. A tensiometer (or "isometer") 188 of conventional or known design is used to test the isometry of the drilled holes. The suture 180 is passed through the tensiometer 188 by a suture passer (not shown). The 2 mm tip 190 on the tensiometer is passed up the tibial drill hole 184 until the slanted surface 192 is firmly seated on the tibial cortex. (See FIG. 13.) The suture 180 is pulled tightly through the drill holes 182 and 184 and fastened securely to the end 194 of the tensiometer 188.

The tensiometer 188 is essentially a spring loaded strain gauge. One of the preferred types of tensiometers which can be used in accordance with the present invention is shown and described in the article entitled "ISOMETRIC PLACEMENT OF SUBSTITUTES FOR THE ANTERIOR CRUCIATE LIGAMENT", by Ben Graf, M.D.

Figure 14:
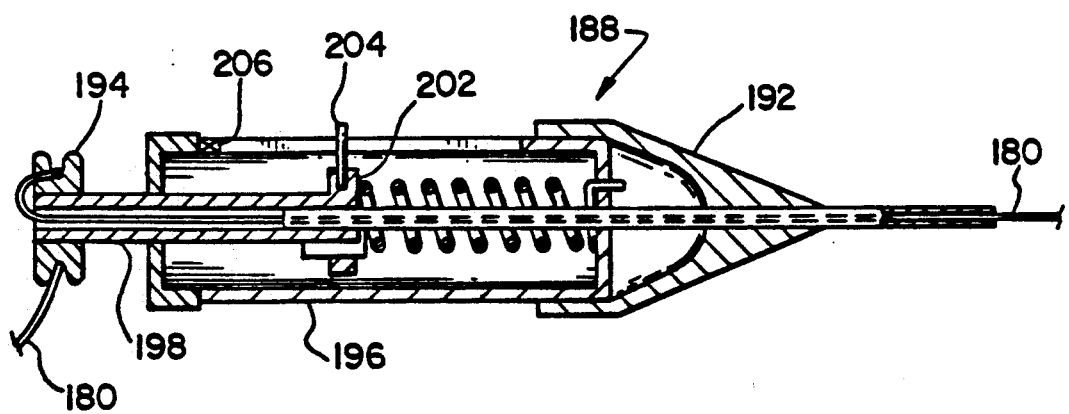
FIG. 14 is a cross-sectional view of the tensiometer shown in FIGS. 12 and 13.

As shown in FIG. 14 (together with FIGS. 12 and 13), the tensiometer 188 has a slanted front surface 192, a housing 196, a plunger member 198 and a coil spring 200. The plunger 198 fits within the housing 196 in a sliding telescopic relationship. The internal end 202 of the plunger is connected to the coil spring 200 which in turn is connected to the inside of the housing. The end 202 also has a locking post 204 which is adapted to slide along slot 206 or be locked in position in a bayonet or "J-shaped" slot 208. The spring 200 biases the member 198 relative to the housing.

A scale 210 in millimeters is arranged along the edge of the slot 206 so readings can be made of the relative position of the post 204. Preferably, the center of the scale at the entrance to the J-shaped slot 208 is set at "zero" so that positive and negative strain gauge readings from the zero point can be read in millimeters depending on the movement of the post during operation of the tensiometer 188.

Once the suture 180 is tightly held in position by the button 186 and tensiometer 188, the tensiometer is unlocked (i.e. the post 204 is moved from the J-shaped slot 208 to the main slot 206). The knee is manually taken through the range of motion from 0°-110° and the excursion of the post 204 on the tensiometer is noted.

If the post movement is less than 1.5 mm then the correct femoral and tibial tunnel sites have been determined. If the readings are not within this range, then additional drill holes are made in the manner as described above and the isometric test is repeated.

Once isometry is obtained, the tensiometer 188 and suture 180, together with the button 186, are removed and the guide pins are replaced in the femoral and tibial drill holes. (This replacement should be checked, especially in patients with soft bones, to be certain that the pins have followed the correct pathways into the joint.)

Figure 15:
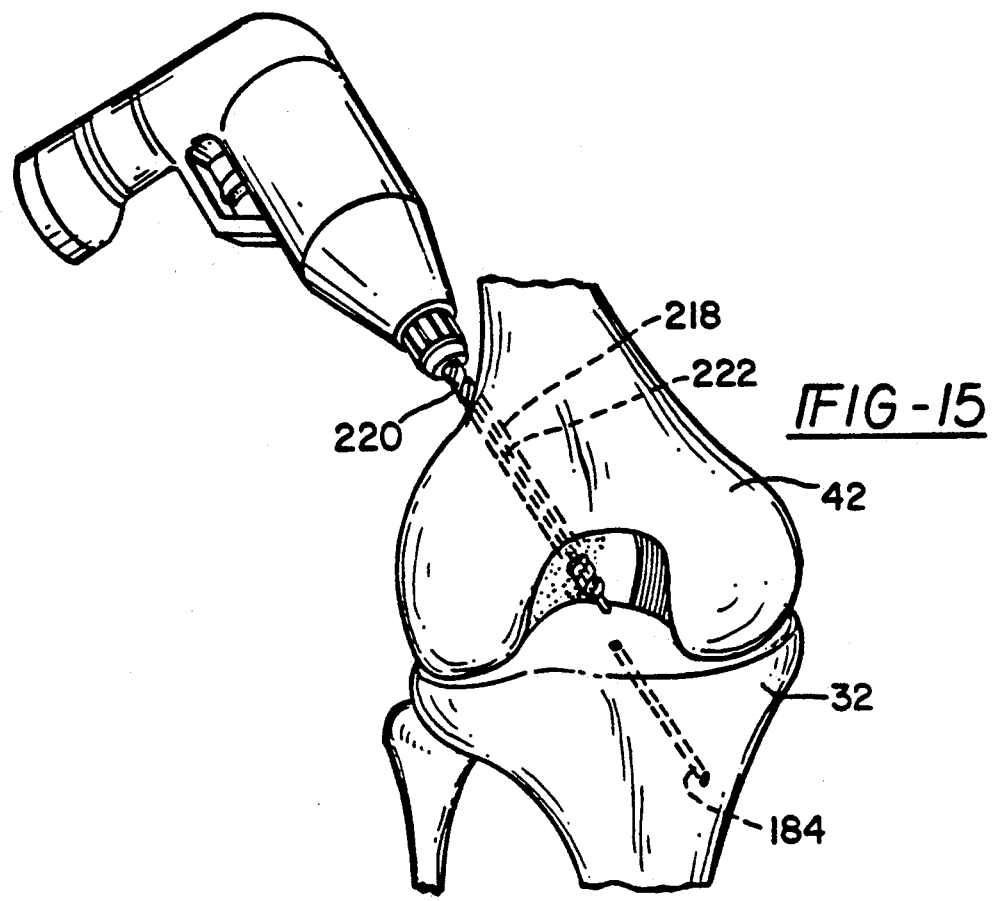
FIG. 15 illustrates the drilling and formation of the femoral tunnel.

The femoral tunnel 218 is then drilled using a properly sized cannulated reamer 220 over the guide pin 222. See FIG. 15. As mentioned earlier, the size of the tunnel is determined based on the snug fit of the double looped tendon graft 52 in a graft sizer. The reamer 220 should be controlled and viewed arthroscopically when it enters the joint to prevent inadvertent damage to the intercondylar contents. Preferably, the reamer is drilled in and out of its passageway 8-10 times in order to make a uniform tunnel. All bone fragments are irrigated from the joint.

Once the tunnel 218 has been formed, the edges or intra articular margins of the tunnel in the joint are smoothed and chamfered with a curved rasp. The rasping should be conservative to avoid changing of the position of the tunnel. The smoothing of the tunnel entrance into the joint prevents abrasion and potential damage to the graft. A properly sized tunnel plug (not shown) is inserted in the femoral tunnel temporarily and the joint is fully distended.

Figure 16:
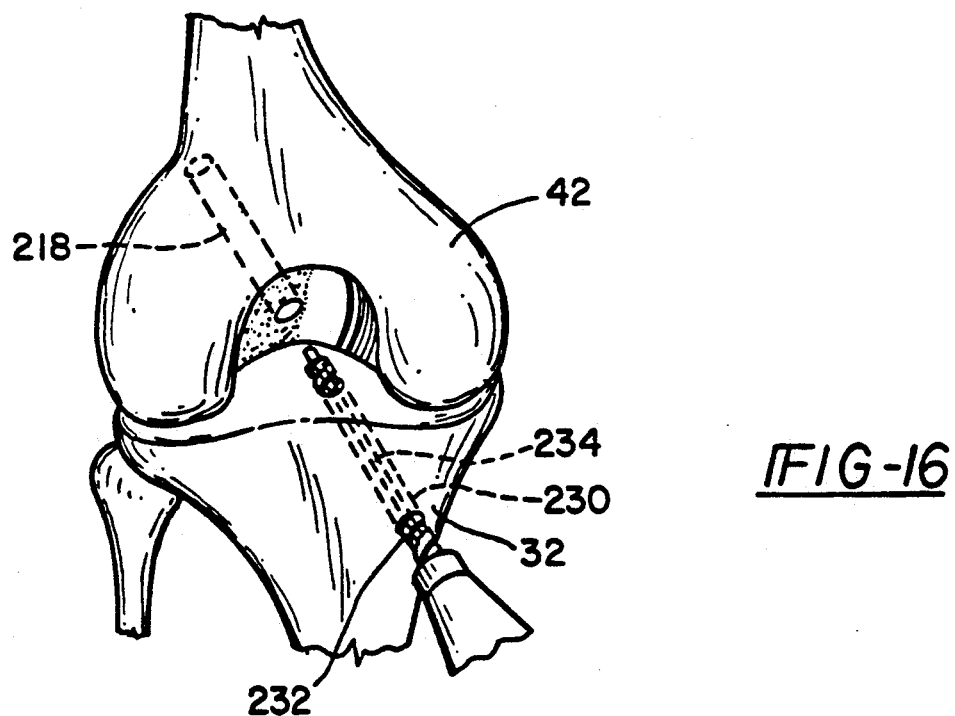
FIG. 16 illustrates the drilling and formation of the tibial tunnel.

The same procedure is used to drill the tibial tunnel 230. This is shown in FIG. 16. A properly sized cannulated reamer 232 is used to drill the tunnel over the guide pin 234. All bone chips and fragments are removed in a conventional manner and the tunnel edges are smoothed and chamfered with a rasp. A temporary hole plug is usually not needed on the tibial side because the ACL remnant at its insertion site seals the hole. A plug can be used if needed or desired, however.

After the two osseous tunnels 218 and 230 are finished, the possible impingement of the intercondylar roof on the substitute ACL graft is checked. This is accomplished by use of a unique calibrated sizer instrument 250 which has an elongated rod 252 and a handle member 254. (See FIGS. 17 and 18.)

The handle member 254 preferably is knurled for ease of grasping and manipulation. In accordance with the invention, it is also possible to provide T-shaped handles or other types of handle members for the sizer instrument.

The rod 252 is graduated with a series of calibrated markings 256 thereon. The markings are in 5 mm increments and are used to determine the placement and positioning of the sizer relative to the tibial tunnel 230.

A sizer member is selected that matches the diameter of the newly drilled tibial tunnel 230. As shown in FIG. 17, the sizer member 250 is inserted in the tunnel so that the end 258 is positioned flush with the end of the tibia. The sizer is first inserted with the knee flexed at about 90°. The depth of the sizer 250 into the tibial tunnel is measured by noting the calibrated markings 256 on the rod 252. The knee, deflated of irrigation fluid, is then brought into maximum hyperextension. This is shown in FIG. 18. The amount of knee extension (angle "A") is measured by observing the angle between the femur and tibia from the side.

An attempt is made to push the sizer 250 into the joint. If the sizer cannot be pushed 25-35 mm into the joint, then notch impingement exists. The calibrated markings 256 are used to determine whether impingement is present.

The effect of untreated notch impingement on ultimate knee extension can be estimated by slowly flexing the knee while trying to advance the sizer into the notch through the tibial tunnel. The flexion angle at which the sizer can be advanced freely into the notch is observed. The difference in knee extension from that point to the point of maximum hyperextension indicates the amount of knee extension that would be lost if the impingement was not corrected.

If the sizer member passes all the way into the back of the notch (e.g. 30 mm mark) with the knee in hyperextension, then there is no impingement and it is unnecessary to cut the roof of the intercondyle notch.

Figure 20:
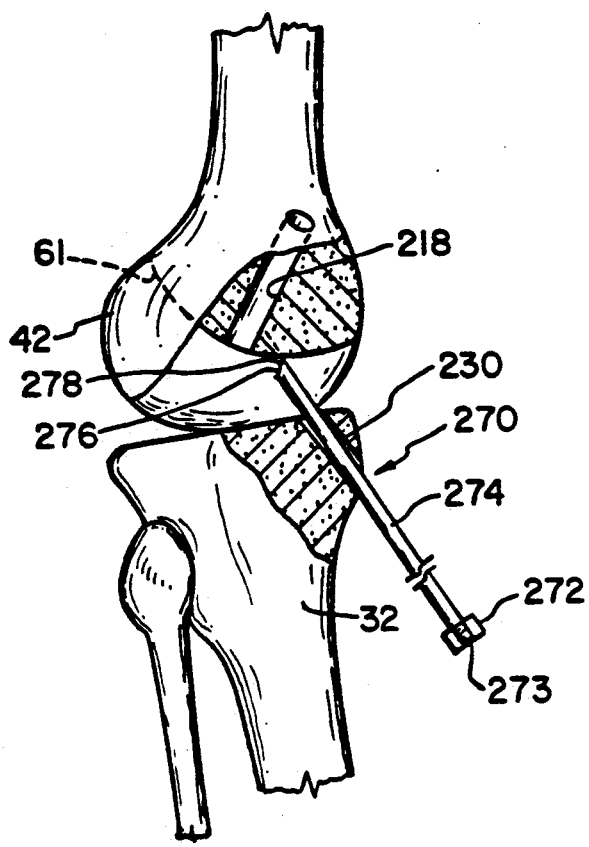

As is usually the case, impingement is determined to exist and a tailored roofplasty must be performed. Bone is removed from along the sagittal depth of the intercondylar roof. Preferably a gouge instrument 270 as shown in FIGS. 19 and 20 is used to mark the location of the required notchplasty on the roof 66 of the intercondylar notch 61 (i.e. "roofplasty"). The gouge has a handle member 272 at one end for ease of grasping and manipulation and an elongated shaft or rod 274. The end 276 of the shaft is angled and has a sharp pointed tip or cutting edge 278 on one side.

In accordance with the invention, the gouge 270 can have any type of handle member 272, such as a T-shaped handle or the like. Also, one side or edge of the handle member is notched or flattened 273 corresponding to the position of the cutting edge on the rod so that the surgeon will be better able to move and manipulate the tip in the joint.

The diameter of the shaft or rod 274 of the gouge instrument 270 is identically sized to match the diameter of the tibial tunnel 230. This allows for accurate marking of the roof impingement.

With the knee maintained in hyperextension, the gouge 270 is passed through the tibial tunnel until the tip 278 abuts the intercondylar notch surface, as shown in FIG. 20. The location of the impingement is marked by striking the gouge with a mallet. The tip (or cutting edge) of the gouge is rotated as the gouge is struck forming an outline of the area of impinging bone which has to be removed. This outline is typically made in the arch formed by the intercondylar roof and lateral wall.

A tailored roofplasty is then performed, removing the outlined bone using one or more conventional hand-held gouges (not shown). Final smoothing and contouring of the roof is accomplished in a conventional manner using standard motorized burrs and hand-held rasps.

After the roofplasty is completed, the knee is again hyperextended and the sizer instrument 250 reinserted into the joint. If the impingement has been successfully eliminated, the sizer will pass unobstructed into and out of the joint and into the femoral tunnel 218. If there are still any obstructions, then additional roofplasty is performed and the sizer instrument inserted and the joint tested again until all of the possible impingement is removed.

In this manner, the possible impingement of the intercondyle roof on the substitute ACL graft is identified, outlined, and quickly and accurately eliminated. Also, the amount of requisite bone removal is confirmed.

All of the possible impingement is removed before the graft is inserted in place which prevents any possible harm or damage to the graft if any impingements are not found until later and further notchplasty has to be performed with the substitute graft in place. Also, the present invention eliminates the need to perform extensive unnecessary protective notchplasty that is sometimes performed by "feel" in an attempt to insure against impingement.

Figure 21:
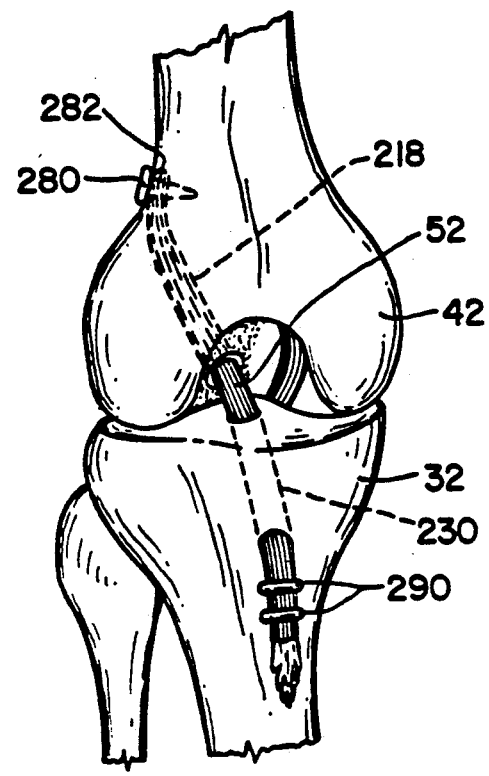
FIGS. 21 and 22 depict the positioning and securing of a tendon graft in accordance with the present invention.
Figure 22:
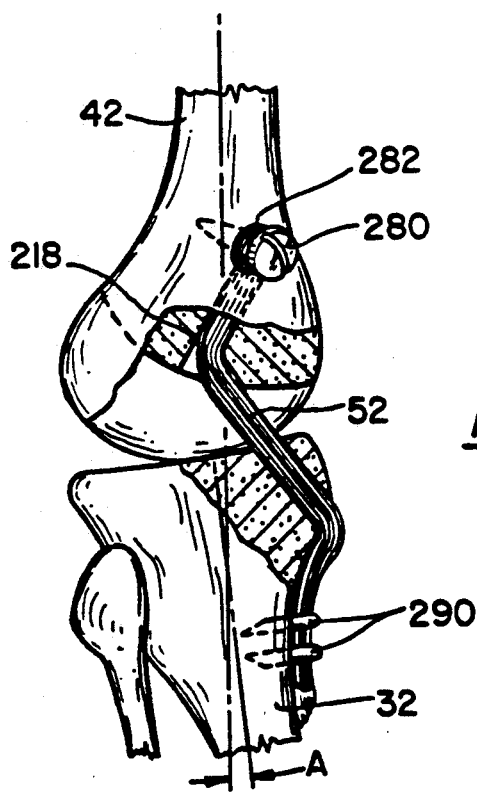

The next step is the placement and securing of the graft in the osseous tunnels. This is shown in FIGS. 21 and 22. The graft 52 (FIG. 3) is inserted in the tunnels and joint and permanently affixed in place.

The graft 52 is passed through the tunnels starting with the tibial tunnel 230. An umbilical tape (not shown) is used to draw the graft 52 through the tunnels. The umbilical tape is first fed through the femoral tunnel 218 and positioned by forceps over the tibial tunnel. A grabber passed up the tibial tunnel 230 pulls the tape through the tibial tunnel where it is attached to the umbilical tape 50 previously looped around the tendons 34 and 46 or to the tendons themselves.

The double-looped graft 52 is then threaded through the tunnels 218 and 230 and pulled through the joint until the end passes out the lateral femoral cortex. About 2 cm of the double-looped tendon is passed all of the way through the femoral tunnel and the end is held in place by a cancellous screw 280.

A 3.2 mm drill hole is made transverse across the femoral metaphysical flair, from lateral to medial at the junction of the linear aspera and the previously cauterized geniculates. The depth of the hole is measured and the hole is tapped for a 6.5 mm cancellous screw 280. The knee is brought into extension and maximally externally rotated. The cancellous screw 280 is placed in the hole with a ceramic ligament washer 282 being provided under the head of the screw. The end of the double-looped graft 52 is looped around the screw and the screw tightened into the lateral cortex.

The sutures 38 which are attached to the other end of the graft 52 and protrude from the tibial tunnel are pulled tightly to remove any redundancies in the composite tendon graft which can occur in snug, well-fitting tunnels. The sutures and graft are held firmly in tension by the surgeon and the junction of the tibial tunnel and graft 52 is palpated. The knee also is taken through a range of motion to check for "pistoning" (i.e. any excursion or movement of the graft in the tunnel). If there is no pistoning between 90° flexion and hyperextension, then the suitability and placement of the ACL graft is assured. For proper graft placement, the graft should slide less than 1 mm out of the tibial tunnel as the knee is brought from 0° to 120° of flexion. This "excursion profile" indicates that the graft will not stretch if it is secured to the tibia with the knee in full extension and external rotation.

The graft 52 is then affixed to the tibia 32 on the external surface of the tibia outside the tibial tunnel 230. Preferably, the end of the graft 52 is stapled in place with one or more serrated low profile bone staples 290. If desired, a small trench or channel (not shown) can be made in the tibia for placement of the end of the tibia. It is also possible in accordance with the present invention to secure the graft 52 or the sutures to a screw in the tibia similar to the manner in which the graft 52 is secured at its other end to the femur. Also, the ends of the graft containing the whip stitches can be trimmed from the graft after it is secured firmly in place.

When the tendons 34 and 46 have been properly harvested for the graft 52, sufficient length of tendon should remain extending out of the tibial tunnel to allow placement of two staples 290. When insufficient graft protrudes, the graft can be secured with one staple and the sutures 38 can be tied to another staple.

After the graft is secured, the knee joint is tested with the Lachman and drawer tests. The knee should be tighter than the uninjured knee.

The graft is also finally examined arthroscopically to check for any impingements. If any are found, they are corrected and removed.

After the graft is fully secured and examined in place, the wounds around the knee are closed and dressed, the tourniquet removed, a leg brace is installed, and appropriate postoperative care is followed.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

What is claimed is:

1. A drill guide for determining the site for and positioning a transverse pin member in a femur, the drill guide comprising:
   a) an elongated bar member;
   b) an aimer member attached to said bar member and extending therefrom and shaped to pass in a posterior direction from said bar member toward the femoral intercondylar notch and having a tip having a notched convexly curved and flattened upper surface shaped to nest with the cartilaginous roof surface of the femoral intercondylar notch; and
   c) a positioning member mounted to said bar member defining a transverse drilling axis passing through a femoral condyle and having a predetermined orientation with respect to said aimer member tip.

2. The drill guide as set forth in claim 1 wherein said aimer member extends in a generally perpendicular direction form said bar member.

3. The drill guide as set forth in claim 1 wherein said positioning member is slidably positioned on said bar member and has a drill sleeve for holding and positioning a drill therein.

4. The drill guide as set forth in claim 3 wherein said drill sleeve is releasably attached to said positioning member.

5. The drill guide as set forth in claim 1 further comprising means for releasably attaching said positioning member to said bar member, whereby said positioning member can be temporarily secured to said bar member at a variety of positions along said bar member.

6. The drill guide as set forth in claim 1 wherein said tip is configured such that a pin member installed in the femur through said positioning member from a side of the femur will be installed immediately adjacent to and not intersecting with said tip in said intercondylar notch.

7. A drill guide for determining the site for and positioning a pin member in a tibia to mark the location of a tibial tunnel for use in replacing an anterior cruciate ligament, the guide member comprising:
   a) an elongated bar member;
   b) a hook member attached to said bar member having an elongated shaft and shaped to pass in a posterior direction toward the femoral intercondylar notch and having a curved tip configured to contact a position pin present within the femoral intercondylar notch and having a notched convexly curved and flattened upper surface shaped to be positioned against the anterior aspect of the intercondylar notch and a concave lower surface adapted to receive and nest with said positioning pin; and
   c) a positioning member mounted to said bar member defining a generally posterior drilling axis passing through the tibia toward said femoral intercondylar notch.

8. The drill guide as set forth in claim 7 wherein said positioning member has a drill sleeve for holding and positioning a drill therein.

9. The drill guide as set forth in claim 8 wherein said drill sleeve is releasably attached to said positioning member.

10. The drill guide as set forth in claim 7 further comprising means for releasably attaching said positioning member to said bar member, whereby said positioning member can be temporarily secured to said bar member at a variety of positions along said bar member.

11. A drilling system for accurately determining the site of the positioning for a tibial tunnel for use in replacing an anterior cruciate ligament with a substitute graft member, said graft member being adapted to be securely positioned in the knee joint in tunnels in the femur and tibia, said system comprising:
   a) a first drill guide for positioning and placing a first pin member transversely in the femur, said drill guide having a first aimer member attached to said first bar member having a tip having a notched convexly curved and flattened upper surface shaped to nest with the cartilaginous roof surface of the femoral intercondylar notch;
   b) a second drill guide for positioning and placing a second pin member in the tibia, said second drill guide having a second elongated bar member and a second aimer member attached to said second bar member having an elongated shaft and a curved tip shaped to contact said first pin member in said femoral intercondylar notch and having a notched convexly curved and flattened upper surface shaped to be positioned against the anterior aspect of the intercondylar notch and a concave lower surface adapted to receive and nest with said first pin member; and
   c) a positioning member for drilling holes, said positioning member sized and configured to be positioned either on said first bar member for using said first drill guide or on said second bar member for using said second drill guide;
   whereby when said positioning member is positioned on said first bar member, said first drill guide is used to position and place said first pin member transversely in said femur, and when said positioning member is positioned on said second bar member, said second drill guide is used to determine the site for the drilling of the tibial tunnel.

12. The drilling system as set forth in claim 11 further comprising means for releasably attaching said positioning member to said first bar member and said second bar member, whereby said positioning member can be positioned and temporarily secured to either of said bar members at a variety of different positions thereon.

13. The drilling system as set forth in claim 11 wherein said positioning member has a drill sleeve for holding and positioning a drill therein.

14. The drilling system as set forth in claim 13 wherein said drill sleeve is releasably attached to said positioning member.

* * * * *

UNITED STATES PATENT AND TRADEMARK OFFICE
CERTIFICATE OF CORRECTION

PATENT NO. : 5,300,077
DATED : April 5, 1994
INVENTOR(S) : Stephen M. Howell

It is certified that error appears in the above-indentified patent and that said Letters Patent is hereby corrected as shown below:

Col. 3, Line 4, "FIG." should be --FIGS.--.

Col. 9, Line 15, "cartilagenous" should be --cartilaginous--.

Col. 10, Line 49, "fu" should be --fulfilled its intended--.

Col. 15, Line 22, Claim 2, "form" should be --from--.

Col. 15, Line 51, Claim 7, "position" should be --positioning--.

Signed and Sealed this

Twelfth Day of September, 1995

Attest:

BRUCE LEHMAN

*Attesting Officer*     *Commissioner of Patents and Trademarks*